US007615534B2

(12) United States Patent
Yoshida et al.

(10) Patent No.: US 7,615,534 B2
(45) Date of Patent: Nov. 10, 2009

(54) ANTIMICROBIAL PEPTIDES AND USE THEREOF

(75) Inventors: Tetsuhiko Yoshida, Nagoya (JP); Yoshinao Yamada, Nagoya (JP); Nahoko Kobayashi, Nagoya (JP); Hiroki Kourai, Tokushima (JP)

(73) Assignee: Toagosei Co., Ltd, Minato-ku (JP)

( * ) Notice: Subject to any disclaimer, the term of this patent is extended or adjusted under 35 U.S.C. 154(b) by 384 days.

(21) Appl. No.: 11/247,376

(22) Filed: Oct. 11, 2005

(65) Prior Publication Data

US 2006/0089488 A1 Apr. 27, 2006

(51) Int. Cl.
*A61K 38/10* (2006.01)

(52) U.S. Cl. ............................ 514/13; 514/12; 530/326

(58) Field of Classification Search ....................... None
See application file for complete search history.

(56) References Cited

U.S. PATENT DOCUMENTS

| | | | | |
|---|---|---|---|---|
| 5,547,939 | A | 8/1996 | Selsted | |
| 5,789,542 | A | 8/1998 | McLaughlin et al. | |
| 5,807,746 | A | 9/1998 | Lin et al. | |
| 5,877,282 | A | 3/1999 | Nadler et al. | |
| 5,962,415 | A | 10/1999 | Nadler | |
| 6,043,339 | A | 3/2000 | Lin et al. | |
| 6,180,604 | B1 | 1/2001 | Fraser et al. | |
| 6,191,254 | B1 | 2/2001 | Falla et al. | |
| 6,303,575 | B1 | 10/2001 | Selsted | |
| 6,476,189 | B1 | 11/2002 | Yamakawa et al. | |
| 2005/0171335 | A1 | 8/2005 | Kourai et al. | |
| 2007/0248584 | A1 * | 10/2007 | Kent | 424/93.72 |

FOREIGN PATENT DOCUMENTS

| | | | |
|---|---|---|---|
| JP | 2001186887 | | 7/2001 |
| WO | WO9926971 | * | 6/1991 |
| WO | 9402610 | | 2/1994 |
| WO | 9636692 | | 11/1996 |
| WO | 9851794 | | 11/1998 |
| WO | 9926971 | | 6/1999 |
| WO | 9929721 | | 6/1999 |
| WO | 9967284 | | 12/1999 |
| WO | 0009553 | | 2/2000 |
| WO | 0059527 | | 10/2000 |
| WO | 0109175 | | 2/2001 |
| WO | 0210201 | | 2/2002 |
| WO | 03091429 | | 11/2003 |
| WO | WO2004056391 | * | 7/2004 |

OTHER PUBLICATIONS

Beven et al, Effects on mollicutes (wall-less bacteria) of synthetic peptides comprising a signal peptide or a membrane fusion peptide, and a nuclear localization sequence (NLS) a comparison with melittin, Biochim Biophys Acta Oct. 23, 1997; 1329(2), pp. 357-369.

Chaloin et al, Ionic Channels formed by a primary amphipathic peptide containing a signal peptide and a nuclear localization sequence, Biochim Biophys Acta Oct. 15, 1998; 1375(1-2), pp. 52-60.

Shai, From innate immunity to de-novo designed antimicrobial peptides, Current Pharmaceutical Design, 2002, vol. 8, No. 9, Apr. 1, 2002, pp. 715-725.

Goode et al, Identification of a novel microtubule binding and assembly domain in the developmentally regulated inter-repeat region of tau, The Journal of Cell Biology, vol. 124 (1994), pp. 769-782.

Goode et al, Functional interactions between the proline-rich and repeat regions of tau enhance microtubule binding and assembly, Molecular Biology of the Cell, vol. 8 (1997), pp. 353-365.

Bergen et al, Assembly of protein into Alzheimer paired helical filaments depends on a local sequence motif forming structure, PNAS, vol. 97, No. 10 (2000), pp. 5129-5134.

Kubota et al, A cis-acting peptide signal in a human immunodeficiency virus type I Rev which inhibits nuclear entry of small proteins, Oncogene, vol. 16 (1998), pp. 1851-1861.

Fang et al, Trans-Dominant Negative HIV Type 1 Rev with Intact Domains of NLS/NOS and NES, AIDS Research and Human Retroviruses, vol. 18, No. 10 (2002), pp. 705-708.

* cited by examiner

*Primary Examiner*—Anish Gupta
(74) *Attorney, Agent, or Firm*—Turocy & Watson, LLP

(57) ABSTRACT

Artificially synthesized antimicrobial peptide that does not occur naturally is provided by the present invention. The antimicrobial peptide includes one unit, two units or more units of amino acid sequence composed of the following 8 amino acid residues:

(R or Q)-(L or F or I)—I—K-(L or F or I or V)-L-Y-Q; and/or, modified sequence composed of said sequence with partial modification.

6 Claims, No Drawings

ANTIMICROBIAL PEPTIDES AND USE THEREOF

CROSS REFERENCES TO OTHER APPLICATIONS

This application is based on Japanese Application No. 2004-224325 filed on Jul. 30, 2004, the entire content of which is hereby incorporated by reference.

TECHNICAL FIELD

The present invention relates to oligopeptide or polypeptide having antimicrobial property (hereinafter, antimicrobial peptide) and comprising independent peptide chains in the form that does not occur naturally, and their utilization. More specifically, the present invention relates to antimicrobial agent (composition) having such antimicrobial peptide as the main component.

BACKGROUND ART

It is generally believed that antimicrobial peptide has a broad antimicrobial spectrum such that drug resistant bacterium hardly appears, and therefore antimicrobial peptide is expected to be used for the purpose of preventing and treating bacterial infectious diseases in human beings and animals or providing antimicrobial properties to products such as food. A large number of antimicrobial peptides have been isolated from various animals and plants to date.

For example, a variety of antimicrobial peptides are disclosed in Japanese Laid-Open Patent Publication No. 2000-63400, Japanese Laid-Open Patent Publication No. 2001-186887, International Publication No. WO98/51794, International Publication No. WO99/26971, International Publication No. WO00/09553, International Publication No. WO00/59527 and International Publication No. WO01/09175. In addition, artificially synthesized antimicrobial peptides, which are designed and created by utilizing known amino acid sequence of which relations with antimicrobial properties have never been discussed, are reported in International Publication No. WO03/91429.

SUMMARY

The present invention provides, without utilizing the developmental approach of antimicrobial agent including the conventional antimicrobial peptides described in the aforementioned publications, new antimicrobial peptides composed of artificially designed amino sequences that are different from peptides existing and functioning as antimicrobial peptides in nature, and polynucleotides encoding such peptides. The present invention also provides antimicrobial agents (pharmaceutical compositions) having such non-natural antimicrobial peptide as the main component.

The antimicrobial peptide provided by the present invention is created by utilizing amino acid sequence included in a polypeptide that is different from the polypeptide serving as antimicrobial peptide in nature. The antimicrobial peptide described herein is an artificially synthesized antimicrobial peptide that does not occur naturally and having an antimicrobial property against at least one type of bacteria. Such antimicrobial peptide includes one unit, two units or more units of at least one amino acid sequence shown in (1) and (2) respectively:

(1) an amino acid sequence composed of the following 8 amino acid residues, (R or Q)-(L or F or I)—I—K-(L or F or I or V)-L-Y-Q (hereinafter, amino acid sequence composed of such 8 amino acid residues is also abbreviated as "8aa sequence" in some cases);

(2) a modified amino acid sequence composed of the amino acid sequence in (1) with partial modification (hereinafter, such sequence is also abbreviated as "modified 8aa sequence" in some cases). It is desirable that a total number of amino acid residues in said one unit, two units or more units of amino acid sequence included in the antimicrobial peptide described herein is 30% or more of a total number of amino acid residues constituting the peptide chain.

The inventors of the present invention focused on nuclear diffusion inhibitory signal (NIS) sequence, specifically, the NIS sequence that is a partial sequence of Rev-protein derived from human immunodeficiency virus (typically, type 1 (HIV-1)) known as a factor which has an effect on viral RNA and regulates virus replication. Two publications related to NIS are as follows:

Satoshi Kubota and Roger J. Pomerantz, *Oncogene*, Vol. 16, pp. 1851-1861 (1998);

Jianhua Fang, Satoshi Kubota and Roger J. Pomerantz, *AIDS RESEARCH AND HUMAN RETROVIRUSES*, Vol. 18 (10), pp. 705-709 (2002).

The inventors of the present invention discovered that peptide including a partial sequence of NIS possesses high antimicrobial property against bacteria or the like, and thereby leading to the accomplishment of the present invention. One of the preferred antimicrobial peptides described herein includes an amino acid sequence composed of at least a part of NIS sequence included in Rev-protein derived from human immunodeficiency virus (HIV), where said amino acid sequence includes an amino sequence shown in said (1) amino acid sequence composed of 8 amino acid residues. The antimicrobial peptide described herein can exhibit high antimicrobial activity against at least one type of bacteria (gram-positive bacteria and/or gram-negative bacteria), or fungi.

The present invention also provides a method for producing the antimicrobial peptide described herein. The method for producing the antimicrobial peptide provided by the present invention includes (1). determining either one type of NIS sequence known as nuclear diffusion inhibitory signal (NIS) sequence included in a Rev-protein derived from human immunodeficiency virus (HIV), or a partial NIS sequence constituting a part of said sequence, said partial NIS sequence including an amino acid sequence composed of the following 8 amino acid residues: (R or Q)-(L or F or I)—I—K-(L or F or I or V)-L-Y-Q; (2). designing a peptide chain such that one unit, two units or more units of said determined sequence and/or a modified sequence composed of said sequence with partial modification is included therein, and a total number of amino acid residues included in said one unit, two units or more units of amino acid sequence is 30% or more of a total number of amino acid residues; and (3). synthesizing said designed peptide chain. In view of designing said peptide chain, it is desirable that said peptide chain is designed such that two, three or more units of said determined sequence and/or said modified sequence are arranged in proximity with each other. Further, in view of designing said peptide chain, it is also desirable that said peptide chain is designed such that a total number of amino acid residues is 100 or less.

The present invention also provides an antimicrobial agent (typically, compositions that can be used in the medical or sanitary fields) including at least one of the antimicrobial peptides described herein and a carrier that can be pharmaceutically acceptable. An antimicrobial agent including an antimicrobial peptide, of which total number of amino acid residues is 100 or less, as the main component is desirable. Antimicrobial agent including peptide having such short peptide chain (thus antimicrobial peptide of relatively low molecular mass) is easy to utilize, and can be a preferred antimicrobial agent for in vivo and/or ex vivo usage.

The present invention also provides an artificially designed polynucleotide that does not occur naturally, and the polynucleotide includes a nucleotide sequence encoding either one of the antimicrobial peptides described herein, and/or a nucleotide sequence complementary to said nucleotide sequence (for example a polynucleotide substantially composed of these sequences).

A desirable polynucleotide will be a polynucleotide including a nucleotide sequence and/or a nucleotide sequence complementary to said nucleotide sequence that encode(s) one amino acid sequence (or a modified sequence composed of the one amino acid sequence with partial modification) selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25 (for example a polynucleotide substantially composed of these sequences).

DETAILED DESCRIPTION

Hereinafter, preferred embodiments of the present invention will be described. The matters, apart from those specifically mentioned in this specification (e.g., primary structure or chain length of antimicrobial peptide), which are necessary for performing the present invention (for example, general matters related to peptide synthesis, polynucleotide synthesis, and preparation of antimicrobial agent (pharmaceutical composition) including peptide as a component), can be considered as matters of design by those skilled in the art based on the conventional technology in the fields of organic chemistry, biochemistry, genetic engineering, protein engineering, molecular biology, pharmaceuticals, medicine, hygieiology and the like. The present invention can be performed based on the contents described in this specification and the common technical knowledge in the field. In the following description, according to circumstances, amino acids are also expressed in the single letter code based on the IUPAC-IUB nomenclature for amino acids.

In this specification, "artificially synthesized antimicrobial peptide that does not occur naturally" refers to antimicrobial peptide whose peptide chain alone does not independently occur in nature, but peptide segment that is artificially produced by chemical synthesis or biosynthesis (i.e., produced based on genetic engineering). In this specification, "antimicrobial peptide" is a term referring to amino acid polymer having a plurality of peptide bonds displaying antimicrobial activity against at least one type of bacteria, and is not limited by the number of the amino acid residue constituting the peptide chain. The antimicrobial peptide in this specification also includes oligopeptides having 10 and below amino acid residues or polypeptides containing more than 10 amino acid residues.

In this specification, "amino acid residue" is a term encompassing N-terminal amino acid of peptide chain and C-terminal amino acid of peptide chain, unless otherwise specified. In this specification, with respect to specific amino acid sequences, "modified sequences (amino acid sequences) formed with partial modification" refers to amino acid sequences formed by substituting, removing or adding (inserting) one, two or three amino acid residue(s) without loosing the antimicrobial property of the specific amino sequences. For example, sequences formed by the so-called conservative amino acid replacement in which one to several amino acid residue(s) is/are conservatively substituted (for example, sequences in which basic amino acid residue is substituted by other basic amino acid residue), or sequences formed by adding (inserting) one or several (generally two to three) amino acid residue(s) to specific amino acid sequences and the like are typical examples included in the "modified sequences (amino acid sequences) formed with partial modification" of this specification.

In this specification, "polynucleotide" is a general term referring to polymer (nucleic acid) in which a plurality of nucleotides are bound by phosphodiester bonds, and is not limited by the number of the nucleotides. The polynucleotide may include DNA fragments and RNA fragments having various lengths. In addition, "artificially designed polynucleotide that does not occur naturally" refers to polynucleotide whose nucleotide chain (total length) alone does not independently occur in nature, but is artificially chemically synthesized or biosynthesized (i.e., produced based on genetic engineering).

The antimicrobial peptide described in this specification is artificially designed peptide that does not occur naturally, and typically, relatively short polypeptides or oligopeptides having 8aa sequence or modified 8aa sequence. The antimicrobial peptide described in this specification refers to peptide segment in which 30% or more of all the amino acid residues constituting the peptide chain is composed of one unit or two or more units of 8aa sequence(s) or modified 8aa sequence(s). Hence the antimicrobial peptide described in this specification can be clearly differentiated from the various naturally occurring polypeptides (peptide chains). Regarding 8aa sequence or modified 8aa sequence, one unit refers to one sequence portion constituting the 8aa sequence or modified 8aa sequence. Therefore, the case where a peptide chain is composed of two units of 8aa sequences means that two sequences independently regarded as 8aa sequence, regardless of whether they are the same type or different types, are present in the peptide chain. Peptides composed of one unit or two units of 8aa sequence(s) (or modified 8aa sequence(s)) are typically preferred embodiments of the antimicrobial peptides described herein (please refer to the following embodiments).

It is desirable for the ratio of the 8aa sequence (or modified 8aa sequence) in the entire amino acid sequence (thus the percentage of the total number of amino acid residues constituting the peptide chain that is accounted by the number of amino acid residues constituting the 8aa sequence or the modified 8aa sequence) to be 30% or more, or more desirably to be 50% or more, or still more desirably to be 70% or more, or particularly desirably to be 80% or more. It is desirable for all the amino acid residues constituting the antimicrobial peptide to be L-amino acid, but a part or all of the amino acid residues may be substituted with D-amino acids as long as the antimicrobial activity is not lost.

The chain length (number of amino acid residues) of the antimicrobial peptide described herein can varies according to the length of the contained 8aa sequence (modified 8aa sequence), and therefore there is no particular limitation. However, it is desirable that the total number of amino acid residues constituting the peptide to be 100 or less, or more desirably to be 50 or less, or particularly desirably to be 20 or less. For example, synthesizing peptide that contains 8 to 15 amino acid residues is easy and can be easily utilized. There is no particular limitation regarding the conformation (three-dimensional structure) of the peptide, as long as the peptide is antimicrobial in the environment in which it is used, but linear or helical peptide is desirable in view of its difficulty in becoming an immunogen (antigen). Peptide having such a shape hardly constitutes epitope. In view of this, it is desirable for antimicrobial peptide applying to an antimicrobial agent to be linear and having a relatively low molecular weight (typically, the number of amino acid residues: 10 to 30; for example, the number of amino acid residues: 10 to 20).

With regard to the 8aa sequence for designing the antimicrobial peptide, a portion of or the entire sequence known as NIS (typically composed of 15 amino acid residues including 8aa sequence), which is derived from Rev protein isolated from various strain of HIV (HIV type 1), is utilized. Alternatively, the antimicrobial peptide (peptide chain) can be easily designed by utilizing a sequence in which the 8aa sequence or/and sequence of other part apart from the 8aa sequence is/are slightly modified (for example, substituting, removing and/or adding one to several (typically two or three) amino acid residue(s)).

Conventionally, specific examples of the amino acid sequence known as NIS, which is derived from Rev protein in type 1 HIV (HIV-1), is disclosed in the aforementioned publication (Kubota et al., *Oncogene*, Vol. 16, pp. 1851-1861 (1998)) as the following 11 types of sequences: EELLKAVRLIKLLYQ (SEQ ID NO: 1) EDLLKAVRLIKFLYQ (SEQ ID NO: 2); EELIRTVRLIKLLYQ (SEQ ID NO: 3); RRAAQAVRLIKLLYQ (SEQ ID NO: 4); EELLQTVRFIKFLYQ (SEQ ID NO: 5); RELLTAVRIIKILYQ (SEQ ID NO: 6); EDLLRTVRLIKVLYQ (SEQ ID NO: 7); ENLLKAIRLIKFLYQ (SEQ ID NO: 8); QQLLQAIQIIKILYQ (SEQ ID NO: 9); EELLKTVRLIKLLYQ (SEQ ID NO: 10); EELLKTVRLIKFLYQ (SEQ ID NO: 11).

With regard to the several desirable antimicrobial peptides, the amino acid sequence including the amino acid sequence (8aa sequence) composed of the aforementioned 8 amino acid residues is an amino acid sequence, or a partial sequence included in such sequence, selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

The amino acid sequences represented by these sequence numbers are typical NIS sequences, and peptide having a sequence including an 8aa sequence selected from these NIS sequences derived from HIV can have high antimicrobial activity.

Peptide including one type or two or more types of such NIS sequence(s) or partial sequence(s) including a sequence composed of at least 8 amino acid residues of the C-terminal (thus, 8aa sequence) is desirable. For example, particularly desirable antimicrobial peptides described herein are peptides including an amino acid sequence or said amino acid sequence with partial modification, said amino acid sequence is selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25.

Alternatively, antimicrobial peptides shown in either one of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25 (Table 1) are desirable. Alternatively, antimicrobial peptides including a sequence shown in either one of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25, in which one or a plurality of amino acid residue(s) is/are conservatively substituted, are desirable. Antimicrobial peptides including such sequences (typically, antimicrobial peptides composed of such sequences) can exhibit high antimicrobial activity against bacteria, particularly against gram-positive bacteria such as *Staphylococcus aureus*.

In several other desirable antimicrobial peptides, 2 units or more of amino acid sequences composed of the aforementioned 8 amino acid residues (8aa sequence) and/or modified sequences derived from partially modifying such sequences (modified 8aa sequence) are arranged in proximity with each other.

When 2 units or more of 8aa sequences and/or modified 8aa sequences are present in a peptide chain, antimicrobial activity can be increased. Antimicrobial peptides of which such sequences are linked with each other in tandem are particularly desirable.

Further, antimicrobial peptides of which at least one of the amino acid residue(s) is/are amidated are desirable. The structural stability (for example, protease resistance) of the antimicrobial peptides can be improved by amidating a carboxyl group of the amino acid residues (typically the C-terminal amino acid of a peptide chain). Antimicrobial peptides of which the total number of amino acid residues constituting the peptide chain is 100 or less are also desirable. Peptides having such short chain length are easily chemically synthesized, and antimicrobial peptides can be easily provided.

The antimicrobial peptides described herein can include partial sequences that are not present in 8aa sequences (or modified 8aa sequences) or NIS sequences as long as the antimicrobial property is not lost. Although there is no specific limitation, sequences that can maintain the three-dimensional shape of 8aa sequences (or modified 8aa sequences) in a peptide chain are desirable for such partial sequences.

Among the antimicrobial peptides described herein, those having relatively short peptide chain can be easily produced easily according to a general chemosynthetic method. For example, either a conventionally known solid-phase synthetic method or liquid-phase synthetic method can be used. A solid-phase synthetic method using Boc (t-butyloxycarbonyl) or Fmoc (9-fluorenylmethoxycarbonyl) as a protective group for the amino group is preferable. For the antimicrobial peptides described herein, peptide chain having a desired amino acid sequence and a modified (e.g., C-terminal amidated) portion can be easily synthesized by a solid-phase synthetic method using a commercially available peptide synthesis apparatus (available from PerSeptive Biosystem, Applied Biosystems or the like).

Alternatively, the antimicrobial peptides can be synthesized biologically based on a genetic engineering approach. This approach is preferable in producing a polypeptide having a relatively long peptide chain. In other words, DNA of a nucleotide sequence (including ATG start codon) that encodes the amino acid sequence of a desired antimicrobial peptide is synthesized. A recombinant vector having a gene construction substance for expression including this DNA and various regulatory elements (including promoter, ribosome binding site, terminator, enhancer, various cis-elements for controlling the expression level) is constructed in accordance with the host cell.

This recombinant vector is transduced into a predetermined host cell (e.g., yeast, insect cell, plant cell, animal (mammalian) cell) by a regular technique, and tissues or organisms including the host cell or the cell are cultured under predetermined conditions. Thus, a desired polypeptide can be expressed and produced in the cell. Then, a polypeptide is isolated from the host cell (from a medium when secreted) and purified, so that a desired antimicrobial peptide can be obtained. Regarding methods for constructing the recombinant vector and methods for transducing the constructed recombinant vector into the host cell, conventional methods in this field can be utilized, and since such methods are not specific features of the present invention, detail descriptions will be omitted.

For example, a fusion protein expression system can be utilized for efficient mass production in a host cell. In other words, a gene (DNA) encoding an amino acid sequence of a desired antimicrobial peptide is chemically synthesized, and the synthesized gene is introduced into a preferred site of a suitable vector for expression of a fusion protein (e.g., a vector for expression of GST (Glutathione S-transferase) fusion protein such as pET series provided by Novagen and pGEX series provided by Amersham Bioscience). Then, the host cell (typically *E. coli*) is transformed by the vector. The obtained transformant is cultured so that a desired fusion protein is prepared. Then, the protein is extracted and purified. Then, the obtained purified fusion protein is cleaved by a predetermined enzyme (protease) and the separated desired peptide fragment (designed antimicrobial peptide) is collected by an affinity chromatography or the like. The antimicrobial peptide can be produced by using such a conventionally known system for expression of a fusion protein (e.g., GST/His system provided by Amersham Bioscience can be utilized).

Alternatively, a template DNA for a cell-free protein synthesis system (i.e., synthesized gene fragment including a nucleotide sequence encoding an amino acid sequence of an antimicrobial peptide) is constructed, and various compounds (ATP, RNA polymerase, amino acids and the like) are used, so that a targeted polypeptide can be synthesized in vitro by using a so-called cell-free protein synthesis system. Regarding the cell-free protein synthesis system, for example, an article by Shimizu et al. (Shimizu et al., *Nature Biotechnology,* 19, 751-755 (2001)), an article of Madin et al. (Madin et al., *Proc. Natl. Acad. Sci. USA,* 97(2), 559-564 (2000)) can be referred to. At the time of filing the present application, a large number of enterprises have already been entrusted with production of polypeptide based on the technologies described in these articles, and kits for cell-free protein synthesis (e.g., PROTEIOS (trademark) Wheat germ cell-free protein synthesis kit available from TOYOBO Co., Ltd. in Japan) are commercially available. Therefore, once an amino acid sequence to be utilized is determined and a peptide chain is designed as described above, then a desired antimicrobial peptide can be easily produced by a cell-free protein synthesis system according to the amino acid sequence. For example, the antimicrobial peptide can be easily produced based on PURESYSTEM (registered trademark) of POST GENOME INSTITUTE CO. LTD. in Japan.

A polynucleotide of a single strand or a double strand including a nucleotide sequence encoding the antimicrobial peptide described herein and/or a nucleotide sequence complementary to said sequence can be produced (synthesized) by a conventionally known method. In other words, a nucleotide sequence corresponding to the amino acid sequence of the antimicrobial peptide can be easily determined and provided by selecting a codon corresponding to each amino acid residue constituting the designed amino acid sequence. Then, once the nucleotide sequence is determined, then a polynucleotide (single strand) corresponding to the desired nucleotide sequence can be easily obtained by utilizing a DNA synthesis machine or the like. Furthermore, a targeted double strand DNA can be obtained by using various enzymatic synthesis means (typically PCR), using the obtained single strand as a template.

The polynucleotide provided by the present invention may be in the form of DNA or RNA (MRNA or the like). The DNA can be provided in the form of a double strand or a single strand. When it is provided in the form of a single strand, it may be in the form of a code chain (sense chain) or may be non-code chain (anti-sense chain) that is complementary thereto. As described above, the polynucleotide can be used as a material for constructing a recombinant gene (expression cassette) for producing an antimicrobial peptide in various host cells or cell-free protein synthesis systems.

According to the present invention, a polynucleotide including a nucleotide sequence encoding an antimicrobial peptide, which contains a novel amino acid sequence and/or a nucleotide sequence complementary to said sequence can be provided. For example, as shown in SEQ ID NO: 18, a peptide composed of amino acid sequence including two, three or more units of 8aa sequence (or modified 8aa sequence) in tandem is provided, and a polynucleotide including a nucleotide sequence encoding such peptide, and/or a nucleotide sequence complementary to said sequence (for example the polynucleotide encoding the antimicrobial peptide of SEQ ID NO: 18) is provided.

For example, an artificially designed polynucleotide that does not occur naturally, encoding a peptide chain composed of 100 or less amino acid residues (desirably about 50 or less, and particularly desirably about 20 or less) is provided. Such polynucleotide includes (or is substantially composed of) a nucleotide sequence encoding an amino acid sequence and/or a nucleotide sequence complementary to said sequence, while said amino acid sequence includes an amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25, or a modified sequence of such amino acid sequence in which one or a plurality of amino acid residue(s) (for example, 2 to 3) is/are substituted conservatively.

In addition, another artificially designed polynucleotide that does not occur naturally is also provided. Such artificially designed polynucleotide includes (or is substantially composed of) a nucleotide sequence and/or a nucleotide sequence complementary to said nucleotide sequence, while said nucleotide sequence encodes an antimicrobial peptide substantially composed of an amino acid sequence shown in SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24 and SEQ ID NO: 25, or a modified sequence of such amino acid sequence in which one or a plurality of amino acid residue(s) (for example, 2 to 3) is/are substituted conservatively.

The antimicrobial peptide described herein has a high antimicrobial activity against at least one type of bacteria, has a relatively broad antimicrobial spectrum, and can be used preferably as the main component of an antimicrobial agent. For example, it can be used for the purpose of treating bacterial infection, sanitizing an external injury, preventing eye diseases, cleaning an oral cavity (gargling), preventing decay of foods, retaining freshness, removing odor, bacteriocide or bacteriostat for the surface of furniture or sanitary equipment and the like.

The antimicrobial agent used for such purposes (i.e. pharmaceutical composition) can include, apart from the antimicrobial peptide as the main component, various carriers that can be pharmaceutically acceptable. Carriers that are generally used as diluent, excipient and the like in peptide medication are desirable. Typically, water or physiological buffering solution is used, but apart from this, various organic solvent such as alcoholic (for example, ethanol) aqueous solution of appropriate concentration, glycerol, non-drying oil such as olive oil can also be used. Alternatively, liposome can also be used. As for secondary component, various filling agents, fillers, binders, moisturizers, surfactants, excipients, pigments, fragrances or the like can be used, depending on the use or the form of the antimicrobial agent.

For the main component of the composition, as long as the antimicrobial property is not lost, apart from the antimicrobial peptide described herein, acid addition salt of the peptide produced by the addition reaction generally used non-organic acid or organic acid according to conventional procedure can be used. Specific examples of acid that can formed such acid addition salt are non-organic acids such as hydrochloric acid, hydrobromic acid, sulfuric acid, phosphoric acid, or organic acids such as formic acid, acetic acid, propionic acid, glycolate acid, lactic acid, pyruvic acid, oxalic acid, succinic acid, maleic acid, maleic acid, tartaric acid, citric acid, benzoic acid, salicylic acid, lower alkane sulfonic acid, benzenesulfonic acid, toluene sulfonic acid. Alternatively, not limited to the acid addition salt described above, other addition salt (for example metal salt) can also be used.

There is no particular limitation regarding the form of the antimicrobial agent. For example, examples of a typical form of medicines for internal or external use include ointment, liquid medicine, suspension, emulsion, aerosol, foam, granule, powder, tablet, and capsule. Furthermore, in order to use it for injection, it can be produced in the form of a freeze dried substance or a granulated substance that is to be dissolved in a physiological saline or a buffering solution (for example PBS) or the like immediately before use so as to prepare a medical fluid. The process itself in which various forms of pharmaceuticals are prepared using materials including the antimicrobial peptide (main component) and various carriers (secondary component) can be performed according to a conventionally known method, and this does not characterize the present invention so that the detailed description thereof will be omitted. As a detailed information source for prescription, for example, "Comprehensive Medicinal Chemistry" edited by Corwin Hansch and published by Pergamon Press (1990) can be referred to.

The antimicrobial agent described herein can be used by a method or a dose in accordance with the form and the purpose thereof. The antimicrobial peptide described herein can maintain a high antimicrobial activity even in a condition where relatively high saline (for example sodium chloride) or organic compound such as serum is present. Hence it is also desirable for the antimicrobial peptide to be used in situations where saline or serum is present. For example, the antimicrobial agent can be administered, as a liquid agent, intravenously, intramuscularly, subcutaneous, intracutaneous or intraperitoneal injection, or by enema to a patient.

Alternatively, the agent can be administered orally when it is in a solid form such as a tablet. When it is used for the purpose of sanitizing (sterilizing) the surface of sanitary ceramic ware or preventing decay of foods, a liquid agent containing a relatively large amount (e.g., 1 to 100 mg/ml) of peptide can be sprayed directly onto the surface of a targeted object, or the surface of a targeted object can be wiped with fabric or paper impregnated with the liquid agent. These are only examples, and the same form and usage as those of conventional peptide antibiotics, agricultural chemicals, medicines or the like having a peptide as a component can be applied. For example, for cancer patients that are subjected to radiotherapy or aids patients, prevention and treatment of bacterial infection are important concerns. The antimicrobial peptide described herein can exhibit high antimicrobial effect against bacteria responsible for infectious diseases (for example gram-positive bacteria such as *Staphylococcus aureus*). Therefore, the antimicrobial peptide of the present invention described herein is useful as a main component of an antimicrobial agent.

The polynucleotide encoding the antimicrobial peptide of the present invention can be used as a material for so-called gene therapy. For example, a gene (typically DNA segment, or RNA segment) encoding the antimicrobial peptide is incorporated into a suitable vector, and transduced into a targeted site, so that the antimicrobial peptide related to the present invention can be expressed constantly in an organism (cell). Therefore, the polynucleotide (DNA segment, RNA segment or the like) encoding the antimicrobial peptide of the present invention is useful as a pharmaceutical for preventing or treating bacterial infection to the above-described patients or the like.

It is important to prevent bacterial infection during culture of skin, bone or various organs in the field of regenerative medicine. The antimicrobial peptide described herein has a very low toxicity with respect to the mammal cells or tissues and can exhibit an antimicrobial effect selectively with respect to the bacterium. Therefore, this is very useful as a pharmaceutical for preventing bacterial infection of a cultured organ or the like. For example, as shown in the examples later, bacterial infection of an organ during culture can be prevented by adding solely the antimicrobial peptide or an antimicrobial agent having the peptide as one of the main components in an appropriate concentration in a culture solution.

Furthermore, with respect to cultured cells or cultured tissues, the polynucleotide encoding the antimicrobial peptide of the present invention can be used as a material used for gene therapy. For example, a gene (typically DNA segment, or RNA segment) encoding the antimicrobial peptide of the present invention is incorporated into a suitable vector, and transduced into a targeted cultured tissue, so that the antimicrobial peptide related to the present invention can be expressed constantly or in a desired period in a cultured tissue (or cell). Therefore, the polynucleotide (DNA segment, RNA segment or the like) encoding the antimicrobial peptide of the present invention is useful as a pharmaceutical for preventing or treating bacterial infection of cultured tissues.

Hereinafter, several examples of the present invention will be described, but they are not intended to limit the present invention.

EXAMPLE 1

Synthesis of Peptides 15 types of polypeptide (samples 1 to 14, comparative sample 1) were produced with a peptide synthesis machine that will be described later. Table 1 shows the amino acid sequences of these polypeptides.

TABLE 1

| Sample No. | Amino Acid Sequence | Total Number of Amino Acid Residues |
|---|---|---|
| sample 1 | VRLLKLLYQ (SEQ ID NO: 12) | 9 |
| sample 2 | VRLIKFLYQ (SEQ ID NO: 13) | 9 |
| sample 3 | VRFIKFLYQ (SEQ ID NO: 14) | 9 |
| sample 4 | VRIIKFLYQ (SEQ ID NO: 15) | 9 |
| sample 5 | IRLIKFLYQ (SEQ ID NO: 16) | 9 |
| sample 6 | RLIKLLYQ (SEQ ID NO: 17) | 8 |

TABLE 1-continued

| Sample No. | Amino Acid Sequence | Total Number of Amino Acid Residues |
|---|---|---|
| sample 7 | RLIKLLYQ RLIKLLYQ (SEQ ID NO: 18) | 16 |
| sample 8 | EELLKAVRLIKLLYQ (SEQ ID NO: 19) | 15 |
| sample 9 | EDLLKAVRLIKFLYQ (SEQ ID NO: 20) | 15 |
| sample 10 | EELIRTVRLIKLLYQ (SEQ ID NO: 21) | 15 |
| sample 11 | RRAAQAVRLIKLLYQ (SEQ ID NO: 22) | 15 |
| sample 12 | RELLTAVRIIKILYQ (SEQ ID NO: 23) | 15 |
| sample 13 | EDLLRTVRLIKVLYQ (SEQ ID NO: 24) | 15 |
| sample 14 | ENLLKAIRLIKFLYQ (SEQ ID NO: 25) | 15 |
| comparative sample 1 | KTKEGVKT (SEQ ID NO: 26) | 8 |

As illustrated in Table 1, samples 1 to 14 each includes an 8aa sequence (underlined portions in Table 1) derived from an NIS sequence shown in either one of SEQ ID NO: 1 to 11. Among these samples, sample 6 is solely composed of one unit of 8aa sequence (RLIKLLYQ), while sample 7 is composed of an 8aa sequence (RLIKLLYQ) arranged in two units tandem. In samples 1 to 5, 1 amino acid residue is added to the N-terminal of the peptide chain, and in sample 8 to 14, 7 amino acid residues are added to the N-terminal of the peptide chain. On the other hand, the comparative sample 1 is a completely unrelated synthesized peptide composed of 8 amino acid residues and does not include such 8aa sequences. Further, the carboxyl group of the C-terminal amino acid (—COOH) in all the samples is amidated (—$CONH_2$).

The above-described polypeptides (each includes 20 or less amino acid residue(s)) were synthesized by a solid synthesis method (Fmoc method) using a commercially available peptide synthesis machine (PEPTIDE SYNTHESIZER 9050 manufactured by PerSeptive Biosystems). As a condensing agent, HATU (Applied Biosystems product) was used, and the resin and the amino acids used in the solid synthesis method were purchased from NOVA biochem. To amidate the C-terminal of the amino acid sequence, “Rink Amide resin (100 to 200 mesh)” was used as the solid carrier.

A peptide chain is elongated from Fmoc-amino acid that is bound to a resin by repeating deprotection reaction and condensation reaction according to the synthesis program of the above-described peptide synthesizing machine, so that a synthesized peptide of a targeted length was obtained. More specifically, Fmoc, which is an amino protecting group of an amino acid, is cleaved and removed with 20% piperidine/dimethylformamide (DMF) (peptide synthesis grade manufactured by KANTO KAGAKU), cleaned with DMF, reacted with 4 eq of Fmoc-amino acid (—OH) each, and cleaned with DMF. This operation was repeated. Then, after all the elongation reaction of the peptide chain was completed, the Fmoc group was cleaved with 20% piperidine/DMF, and the above-described reaction product was cleaned with DMF and methanol in this order.

After solid synthesis, the synthesized peptide chain and the resin were both transferred to a centrifuge tube, and 1.8 mL of ethanediol, 0.6 mL of m-cresol, 3.6 mL of thioanisole, and 24 mL of trifluoroacetic acid were added thereto, and then the mixture was stirred at room temperature for two hours. Thereafter, resin bound to the peptide chain was filtrated and removed. Then, cooled ethanol was added to the filtrate, and a peptide precipitate was obtained by cooling with iced water. Thereafter, the supernatant was discarded by centrifugation (for five minutes at 2500 rpm). Cool diethyl ether was again added to the precipitate and stirred sufficiently, and then centrifugation was performed in the same conditions as above. This process of stirring and centrifugation was repeated in total of three.

The obtained peptide precipitate was vacuum-dried and purified with a high speed liquid chromatography (Waters 600 manufactured by Waters Corp.). More specifically, pre-column (Guard-Pak Delta-pak C18 A300 manufactured by Nippon Waters) and C18 reverse phase column (XTerra (registered trademark) column, MS C18, 5 μm, 4.6×150 mm manufactured by Nippon Waters) were used, and a mixed solution of 0.1% trifluoroacetic acid aqueous solution and 0.1% trifluoroacetic acid acetonitrile solution was used as an eluent. In other words, separation and purification were performed for 30 to 40 minutes using the above-described columns at a flow rate of 1.5 mL/min while increasing over time the amount of the trifluoroacetic acid acetonitrile solution contained in the eluent (providing the concentration gradient from 10% to 80% in volume ratio). The peptide eluted from the reverse phase column was detected at a wavelength of 220 nm using an ultraviolet ray detector (490E Detector manufactured by Waters) and shown on a recording chart as the peaks.

The molecular weight of each eluted polypeptide was determined, using Voyager DE RP (trademark) manufactured by PerSeptive Biosystems, based on MALDI-TOF MS (Matrix-Assisted Laser Desorption Time of Flight Mass Spectrometry). As a result, it was confirmed that the targeted polypeptide was synthesized and purified.

EXAMPLE 2

Antimicrobial Activity of Synthesized Peptides

Regarding the antimicrobial peptide in each of samples 1 to 14, the antimicrobial activities (minimum inhibitory concentration: MIC) with respect to gram-positive bacteria (*Staphylococcus aureus* IFO 12732) were determined, as described below, by a liquid medium dilution technique using a 96-well microplate. *Staphylococcus aureus* bacteria are inoculated from a preservation medium to an agar plate medium (“Muller Hinton Agar” manufactured by DIFCO), and thereafter stationary cultured for 18 hours at 37° C. Cultured bacteria were scratched twice using a disposable loop, and gathered bacteria were suspended in 5 mL of physiological saline. The $OD_{660}$ value of the bacterial suspension derived from diluting the suspension 10 times with physiological saline was determined. The bacterial suspension used in the following tests was prepared by utilizing physiological saline, such that its $OD_{660}$ value was 0.1 (therefore, bacteria concentration: approximately $2\times10^7$ cells/mL).

Each peptide sample derived by the above-described method was dissolved with sterile distilled water, which served as a carrier in the present example, to prepare a drug of predetermined concentration. More specifically, an appropriate amount of peptide sample were added into an Eppendorf (registered trademark) tube with an appropriate capacity, and such peptide sample were dissolved with sterile distilled water to prepare 2 mM of drug (peptide solution). The derived drug was appropriately diluted, and each diluent of approximately 50 μM to approximately 0.39 μM was prepared. Thereafter, each diluent was respectively introduced into the well of a polystyrene 96-round-bottom-well microplate prepared in advance. Next, 5 μL of the bacterial suspension having 0.1 $OD_{660}$ was added (test bacteria quantity: approximately $1\times10^6$ cells/mL) respectively to each well containing the diluent of each concentration. The microplate was then incubated in an incubator at 37° C., and the presence of bacteria was evaluated based on the turbidity 24 hours later. The minimum drug concentration (peptide concentration), in which an increased in turbidity caused by bacteria was not detected at the time of measurement, was defined as MIC (unit: μM) in the present example. The results are illustrated in Table 2.

TABLE 2

| | Antimicrobial Activities (μM) |
|---|---|
| Sample No. | *S. aureus* (24 hours later) |
| Sample 1 | 50 |
| Sample 2 | 12.5 |
| Sample 3 | 25 |
| Sample 4 | 25 |
| Sample 5 | 25 |
| Sample 6 | 25 |
| Sample 7 | 6.25 |
| Sample 8 | 25 |
| Sample 9 | 25 |
| Sample 10 | 25 |
| Sample 11 | 6.25 |
| Sample 12 | 25 |
| Sample 13 | 50 |
| Sample 14 | 6.25 |
| Comparative Sample 1 | No Activity |

As clearly illustrated in the results shown in Table 2, all antimicrobial peptides having 8aa sequence (samples 1 to 14) exhibited high antimicrobial activities. On the contrary, no antimicrobial activity was detected in the comparative peptide (comparative sample 1) composed of 8 amino acid residues. More specifically, by comparing the peptide (sample 6) having one unit of 8aa sequence (RLIKLLYQ: SEQ ID NO: 17), which is present in the C-terminal of NIS sequence derived from HIV-1, with the peptide (sample 7) having two units of the same 8aa sequence, it has been identified that antimicrobial activities can be increased by repeatedly including plurality of units of 8aa sequence (or modified 8aa sequence).

EXAMPLE 3

Preparation of Granules

After 50 mg of polypeptide of the sample 1 were mixed with 50 mg of crystallized cellulose and 400 mg of lactose, 1 mL of a mixed solution of ethanol and water was added and the mixture was kneaded. This kneaded product was granulated according to a regular method, and thus a granule having the antimicrobial peptide as the main component was obtained.

Specific examples of the present invention have been described above, but they are only illustrative and not limiting the scope of the claims. All changes and modifications from the specific examples illustrated above are intended to be embraced in the techniques disclosed in the appended claims. The technical elements described in the specification can exhibit technical usefulness, either alone or in combination, and combinations are not limited to those described in the claims as filed. The techniques illustrated in the specification can achieve a plurality of purposes at the same time, and achieving only one of them has technical usefulness.

What is claimed is:

1. An artificially synthesized antimicrobial peptide having an antimicrobial property against at least one type of bacteria, wherein the antimicrobial peptide comprises an amino acid sequence composed of at least a part of a nuclear diffusion inhibitory signal (NIS) sequence included in a Rev-protein derived from human immunodeficiency virus (HIV), wherein said amino acid sequence is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11; and the total number of amino acid residues is 20 or fewer.

2. An artificially synthesized antimicrobial peptide having an antimicrobial property against at least one type of bacteria, wherein the antimicrobial peptide comprises an amino acid sequence composed of 8 amino acid residues:

R-L-I-K-L-L-Y-Q (SEQ ID NO: 17); and the total number of amino acid residues is 20 or fewer.

3. The peptide according to claim 1, wherein at least one amino acid residue is amidated.

4. An antimicrobial agent comprising:

an antimicrobial peptide having an antimicrobial property against at least one type of bacteria, wherein said peptide comprises an amino acid sequence composed of at least a part of a nuclear diffusion inhibitory signal (NIS) sequence included in a Rev-protein derived from human immunodeficiency virus (HIV), wherein said amino acid sequence is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11, the total number of amino acid residues is 20 or fewer, and a carrier that can be pharmaceutically acceptable.

5. An antimicrobial agent comprising:

an antimicrobial peptide having an antimicrobial property against at least one type of bacteria, wherein the antimicrobial peptide comprises an amino acid sequence composed of 8 amino acid residues:

R-L-I-K-L-L-Y-Q (SEQ ID NO: 17);

the total number of amino acid residues is 20 or fewer, and a carrier that can be pharmaceutically acceptable.

6. The antimicrobial agent according to claim 4, wherein at least one amino acid residue included in the antimicrobial peptide is amidated.

* * * * *

SEQUENCE LISTING

```
<160> NUMBER OF SEQ ID NOS: 26

<210> SEQ ID NO 1
<211> LENGTH: 15
<212> TYPE: PRT
<213> ORGANISM: Human immunodeficiency virus type 1

<400> SEQUENCE: 1

Glu Glu Leu Leu Lys Ala Val Arg Leu Ile Lys Leu Leu Tyr Gln
1               5                   10                  15


<210> SEQ ID NO 2
<211> LENGTH: 15
<212> TYPE: PRT
<213> ORGANISM: Human immunodeficiency virus type 1

<400> SEQUENCE: 2

Glu Asp Leu Leu Lys Ala Val Arg Leu Ile Lys Phe Leu Tyr Gln
1               5                   10                  15


<210> SEQ ID NO 3
<211> LENGTH: 15
<212> TYPE: PRT
<213> ORGANISM: Human immunodeficiency virus type 1

<400> SEQUENCE: 3

Glu Glu Leu Ile Arg Thr Val Arg Leu Ile Lys Leu Leu Tyr Gln
1               5                   10                  15
```

-continued

```
<210> SEQ ID NO 4
<211> LENGTH: 15
<212> TYPE: PRT
<213> ORGANISM: Human immunodeficiency virus type 1

<400> SEQUENCE: 4

Arg Arg Ala Ala Gln Ala Val Arg Leu Ile Lys Leu Leu Tyr Gln
1               5                   10                  15


<210> SEQ ID NO 5
<211> LENGTH: 15
<212> TYPE: PRT
<213> ORGANISM: Human immunodeficiency virus type 1

<400> SEQUENCE: 5

Glu Glu Leu Leu Gln Thr Val Arg Phe Ile Lys Phe Leu Tyr Gln
1               5                   10                  15


<210> SEQ ID NO 6
<211> LENGTH: 15
<212> TYPE: PRT
<213> ORGANISM: Human immunodeficiency virus type 1

<400> SEQUENCE: 6

Arg Glu Leu Leu Thr Ala Val Arg Ile Ile Lys Ile Leu Tyr Gln
1               5                   10                  15


<210> SEQ ID NO 7
<211> LENGTH: 15
<212> TYPE: PRT
<213> ORGANISM: Human immunodeficiency virus type 1

<400> SEQUENCE: 7

Glu Asp Leu Leu Arg Thr Val Arg Leu Ile Lys Val Leu Tyr Gln
1               5                   10                  15


<210> SEQ ID NO 8
<211> LENGTH: 15
<212> TYPE: PRT
<213> ORGANISM: Human immunodeficiency virus type 1

<400> SEQUENCE: 8

Glu Asn Leu Leu Lys Ala Ile Arg Leu Ile Lys Phe Leu Tyr Gln
1               5                   10                  15


<210> SEQ ID NO 9
<211> LENGTH: 15
<212> TYPE: PRT
<213> ORGANISM: Human immunodeficiency virus type 1

<400> SEQUENCE: 9

Gln Gln Leu Leu Gln Ala Ile Gln Ile Ile Lys Ile Leu Tyr Gln
1               5                   10                  15


<210> SEQ ID NO 10
<211> LENGTH: 15
<212> TYPE: PRT
<213> ORGANISM: Human immunodeficiency virus type 1

<400> SEQUENCE: 10

Glu Glu Leu Leu Lys Thr Val Arg Leu Ile Lys Leu Leu Tyr Gln
1               5                   10                  15
```

-continued

```
<210> SEQ ID NO 11
<211> LENGTH: 15
<212> TYPE: PRT
<213> ORGANISM: Human immunodeficiency virus type 1

<400> SEQUENCE: 11

Glu Glu Leu Leu Lys Thr Val Arg Leu Ile Lys Phe Leu Tyr Gln
1               5                   10                  15


<210> SEQ ID NO 12
<211> LENGTH: 9
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 12

Val Arg Leu Ile Lys Leu Leu Tyr Gln
1               5


<210> SEQ ID NO 13
<211> LENGTH: 9
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 13

Val Arg Leu Ile Lys Phe Leu Tyr Gln
1               5


<210> SEQ ID NO 14
<211> LENGTH: 9
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 14

Val Arg Phe Ile Lys Phe Leu Tyr Gln
1               5


<210> SEQ ID NO 15
<211> LENGTH: 9
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 15

Val Arg Ile Ile Lys Ile Leu Tyr Gln
1               5


<210> SEQ ID NO 16
<211> LENGTH: 9
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 16

Ile Arg Leu Ile Lys Phe Leu Tyr Gln
1               5
```

-continued

<210> SEQ ID NO 17
<211> LENGTH: 8
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 17

Arg Leu Ile Lys Leu Leu Tyr Gln
1 5

<210> SEQ ID NO 18
<211> LENGTH: 16
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 18

Arg Leu Ile Lys Leu Leu Tyr Gln Arg Leu Ile Lys Leu Leu Tyr Gln
1 5 10 15

<210> SEQ ID NO 19
<211> LENGTH: 15
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 19

Glu Glu Leu Leu Lys Ala Val Arg Leu Ile Lys Leu Leu Tyr Gln
1 5 10 15

<210> SEQ ID NO 20
<211> LENGTH: 15
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 20

Glu Asp Leu Leu Lys Ala Val Arg Leu Ile Lys Phe Leu Tyr Gln
1 5 10 15

<210> SEQ ID NO 21
<211> LENGTH: 15
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 21

Glu Glu Leu Ile Arg Thr Val Arg Leu Ile Lys Leu Leu Tyr Gln
1 5 10 15

<210> SEQ ID NO 22
<211> LENGTH: 15
<212> TYPE: PRT
<213> ORGANISM: Artificial Sequence
<220> FEATURE:
<223> OTHER INFORMATION: Designed antimicrobial peptide containing a terminal amide group -continued

<400> SEQUENCE: 22

Arg Arg Ala Ala Gln Ala Val Arg Leu Ile Lys Leu Leu Tyr Gln
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 23

Arg Glu Leu Leu Thr Ala Val Arg Ile Ile Lys Ile Leu Tyr Gln
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 24

Glu Asp Leu Leu Arg Thr Val Arg Leu Ile Lys Val Leu Tyr Gln
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Designed antimicrobial peptide containing a terminal amide group

<400> SEQUENCE: 25

Glu Asn Leu Leu Lys Ala Ile Arg Leu Ile Lys Phe Leu Tyr Gln
1 5 10 15

<210> SEQ ID NO 26
<211> LENGTH: 8
<212> TYPE: PRT
<213> ORGANISM: Artificial Sequence
<220> FEATURE:
<223> OTHER INFORMATION: Designed peptide containing a terminal amide group

<400> SEQUENCE: 26

Lys Thr Lys Glu Gly Val Lys Thr
1 5